United States Patent [19]

Sardisco et al.

[11] 4,303,610
[45] Dec. 1, 1981

[54] TEST KIT FOR FIELD ANALYSIS OF PLANT TISSUE MAGNESIUM AND CALCIUM

[75] Inventors: John B. Sardisco; Carroll O. Phillips, both of Shreveport, La.

[73] Assignee: Pennzoil Company, Houston, Tex.

[21] Appl. No.: 150,710

[22] Filed: May 19, 1980

[51] Int. Cl.³ .................................................. G01N 31/16
[52] U.S. Cl. .................................. 422/61; 23/230 R; 422/101; 422/104
[58] Field of Search .......................... 422/61, 101, 104; 23/230 R

[56] References Cited

U.S. PATENT DOCUMENTS

| | | |
|---|---|---|
| 1,910,236 | 5/1933 | Butler . |
| 3,121,613 | 2/1964 | Bittner .............................. 23/230 R |
| 3,203,540 | 8/1965 | Kalt et al. . |
| 3,798,000 | 3/1974 | Helger .............................. 23/230 R |
| 4,126,417 | 11/1978 | Edwards .............................. 422/61 |
| 4,174,202 | 11/1979 | Simpson .............................. 23/230 R |

OTHER PUBLICATIONS

"Instruction for Soil Calcium and Magnesium Test Kit, Model 14855", Hach Chemical Company.

Primary Examiner—William F. Smith
Attorney, Agent, or Firm—Lowe, King, Price & Becker

[57] ABSTRACT

A test kit for field analysis of plant tissue magnesium and calcium contains a cork borer for sampling plant tissue, a grinder for particulating the plant tissue sample, and a funnel holder that is capable of being attached to the test kit container. Furthermore, the test kit contains a syringe that is attached to the exit end of a filtration funnel, with the attachment being through the intermediacy of a tube. Attachment of the syringe to the filtration funnel enables vacuum filtration to be carried out in the field.

13 Claims, 2 Drawing Figures

TEST KIT FOR FIELD ANALYSIS OF PLANT TISSUE MAGNESIUM AND CALCIUM

FIELD OF THE INVENTION

This invention relates to a portable test kit for field analysis of plant tissue. More particularly, the invention relates to a test kit for analysis of plant tissue magnesium and calcium in the field.

Background Art

In the prior art, portable test kits are known, as illustrated by U.S. Pat. Nos. 3,203,540 to Kalt et al, 1,910,236 to Butler, 4,126,417 to Edwards and 4,174,202 to Simpson. The test kit of Kalt et al is used for testing blood. This kit provides a holder for funnel 44, with the holder being provided by an upstanding tubular boss 42 that is formed on the top wall 16 of base member 4 of the kit container. However, it does not appear that this funnel holder is intended to function as a holder when funnel 44 is in use. The Edwards test kit is comprised of a stick having a pH-testing coating on one side and a nitrate-testing coating on the other side. This kit is used for testing soil. The Simpson test kit is used for testing liquids for hydrogen sulfide content.

It is also known to titrate calcium in the presence of magnesium, with U.S. Pat. No. 3,798,000 to Helger being exemplary thereof. Helger relates to the colorimetric determination of calcium in various fluids that include the fluid extract from incinerated spinach leaves. In the Helger patent there is used a buffer system that consists essentially of a mixture of amidosulfonic acid, disodium tetraborate and alkali carbonate, and an indicator reagent that is phthalein purple, eriochrome blue SE or alizarin. In order to mask the magnesium ions, 8-hydroxyquinoline sulfate is preferably added to the indicator reagent. Also illustrative is U.S. Pat. No. 3,121,613 to Bittner, which titrates calcium in the presence of magnesium using an alkaline borate buffer and Eriochrome Blue Black R-methyl red indicator and ethylene glycol bis($\beta$-aminoethyl ether)-N,N'-tetraacetic acid (EGTA). This prior art is also illustrated by a Soil Calcium and Magnesium Test Kit, Model 14855, sold by Hach Chemical. This kit contains two mixing bottles with an indicator mark at the 10 ml volume level, a measuring tube, a graduated vial with a 25 ml mark, a resin for demineralizing water, a gravity filtration funnel, ethylene diamine tetraacetic acid (EDTA), 8.0 N potassium hydroxide, a calcium ion indicator reagent for use in the presence of complexed magnesium ions (known as CalVer ®II powder pillows) and a calcium and magnesium ion indicator reagent (known as UniVer ®III powder pillows).

However, these test kits and other prior art test kits of which we are aware are deficient because they do not permit the field analysis of the magnesium and calcium content of plant tissue; do not contain implements such as a cork borer for sampling plant tissue and a grinder for particulating the plant tissue sample; do not provide a funnel holder that is capable of being attached to the container for the test kit, and a syringe with an attached tube that is attached to the exit end of the filtration funnel to enable vacuum filtration to be carried out in the field; or do not provide for decolorization of an aqueous solution so that a colorimetric indicator may be used.

Disclosure of the Invention

It is accordingly one object of the present invention to provide a portable test kit for field analysis of the magnesium and calcium content of plant tissue.

A further object of the present invention is to provide a test kit containing implements such as a cork borer for sampling plant tissue and a grinder for particulating the plant tissue sample.

An even further object is to provide a test kit containing a funnel holder that is capable of being attached to the container for the test kit, and a syringe with an attached tube that is attached to the exit end of the filtration funnel to enable vacuum filtration to be carried out in the field.

A still further object is to provide a test kit that permits decolorization of an aqueous solution so that a colorimetric indicator may be used.

Other objects and advantages of the present invention will become apparent as the description thereof proceeds.

In satisfaction of the foregoing objects and advantages, there is provided by this invention a portable test kit for field analysis of the magnesium and calcium content of plant tissue. This kit comprises:

a test kit container having a base member, a cover member and a means that maintains said cover member vertical when said container is fully opened;

means for sampling plant tissue;

means for particulating the plant tissue sample;

at least one reservoir container into which the particulated plant tissue is transferred, the transfer being accomplished by use of a measured quantity of a deionized aqueous solvent whereby there is formed in said reservoir container an aqueous mixture of said particulated plant tissue;

demineralizing means for forming said deionized aqueous solvent from an aqueous solvent;

at least one reservoir vial having a lid means, into which said aqueous mixture is transferred from said reservoir container;

means for decolorizing a liquid sample, a part of said decolorizing means being chargeable to said reservoir vial to remove the color from said aqueous mixture;

means for filtering the decolorized aqueous mixture;

means for supporting said filtering means during filtration, said supporting means being directly attachable to said cover member;

means for exerting a vacuum on the decolorized aqueous mixture during filtration, and for collecting the aqueous filtrate;

at least two mixing vials each having an indicator line, into which there is transferred from said vacuum-exerting and filtrate-collecting means a quantity of said aqueous filtrate sufficient to fill each mixing vial to said indicator line;

at least one means for buffering said aqueous filtrate, said buffering means rendering magnesium ions unavailable during calcium ion titration; a portion of said buffering means being chargeable to one of said at least two mixing vials containing said aqueous filtrate;

at least one means for colorimetrically indicating the presence of calcium ions and being a first indicating means; a portion of said first indicating means being chargeable to said one of said at least two mixing vials, and imparting said aqueous filtrate with a first color in the presence of calcium ions and with a second color in the absence of calcium ions;

at least one means for titrating the quantity of calcium ions present, a portion of said calcium ion titrating means being introduceable into said one of said at least two mixing vials, into which said portion of said buffer means and said portion of said first indicator means is charged;

at least one means for colorimetrically indicating the presence of both calcium and magnesium ions and being a second indicator means; a portion of said second indicator means being introduceable into the other of said at least two mixing vials containing said aqueous filtrate, and imparting said aqueous filtrate with one color in the presence of calcium and magnesium ions and with another color in the absence of calcium and magnesium ions; and at least one means for titrating the quantity of both calcium and magnesium ions present, a portion of said calcium and magnesium ion titrating means being chargeable to said other of said at least two mixing vials, into which said portion of said second indicating reagent is introduced.

BEST MODE FOR CARRYING OUT THE INVENTION

Figure 1:
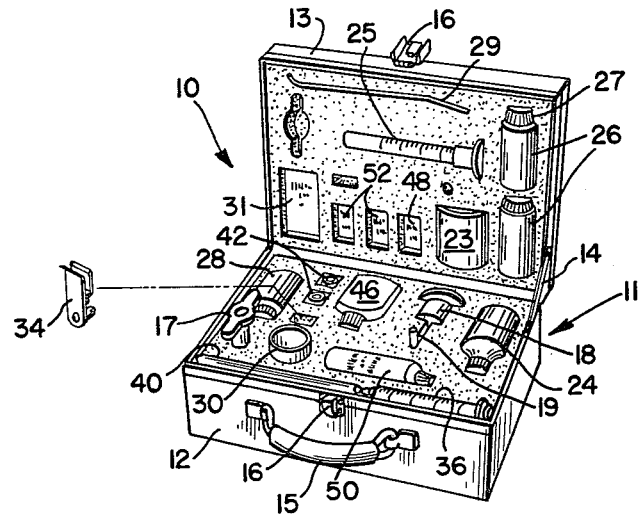
FIG. 1 is a perspective view of the test kit of the present invention with the cover thereof in an open position, showing the testing implements and reagent bottles in place except for the funnel holder.
Figure 2:
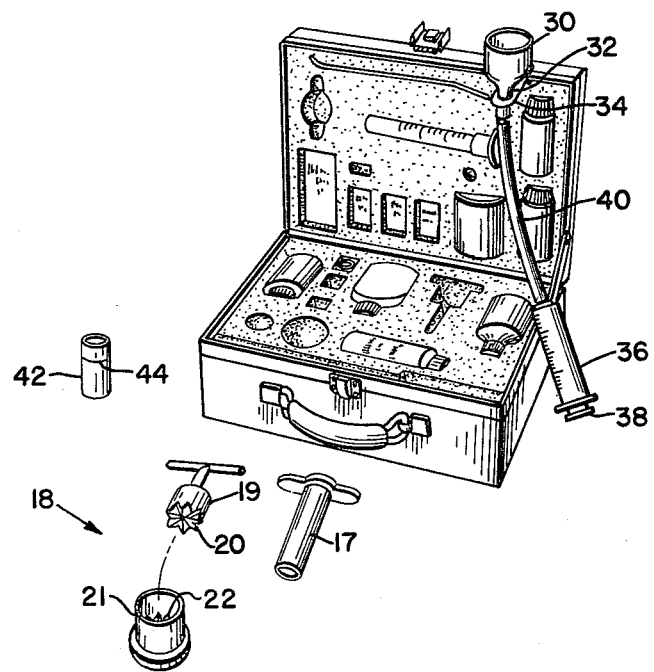
FIG. 2 is a perspective view of the test kit of FIG. 1 showing some of the testing implements removed from the kit and several implements as used, with the reamer shown removed from the grinder cup.

Referring to FIGS. 1 and 2, a test kit 10, in accordance with the present invention, comprises a test kit container 11 having a base member 12, a cover member 13, and a hinge 14 that maintains the cover member vertical when the container is fully opened. The test kit preferably has a handle 15 and a snap lock 16.

Inside test kit container 11, the testing implements and reagent bottles used in field analysis of the magnesium and calcium content of plant tissue are stored. The plant tissue used in the analysis is a plant leaf. A plant is not analyzed for magnesium after the fruit is formed.

Cork borer 17 is used to take plugs of plant tissue from the plant being analyzed. This implement is advantageously a #14 borer. When a #14 borer is used, about 16 to 20 leaf plugs are required to form a suitable sample size of about 1.0 gram. Thicker leaves require a fewer number of plugs to form the sample than thinner leaves require. The plant tissue samples are ground thoroughly in a grinder such as grinder 18, which is novel and disclosed in the copending patent application of Jerry W. Moore and James Allen, filed on the same date as this application, and entitled "Grinding Apparatus", and assigned Ser. No. 150,711. Grinder 18 is comprised of a reamer 19 having V-shaped teeth 20 and of a cup 21, the inner bottom surface 22 of which is formed with teeth having an identical V-shaped configuration. The ground plant tissue is washed from grinder 18 into beaker 23 using a measured quantity of a deionized aqueous solvent, which is advantageously deionized water. About 30 ml of deionized water is useful for this purpose. Transfer of the ground plant tissue may be assisted by scraping some of the tissue from grinder 18 and then washing grinder 18 with the dieonized aqueous solvent. Container 11 contains either deionized water or a resin 24 for demineralizing water, and contains a graduated flask 25 for measuring the 30 ml volume.

When this transfer step is completed, beaker 23 contains an aqueous mixture of the ground plant tissue. This aqueous mixture is then poured from beaker 23 into bottle 26 having a lid 27. A small amount of decolorizing material such as decolorizing carbon 28 is added to bottle 26 to remove the color from the aqueous mixture. Using microspatula 29, about two scoops of decolorizing carbon 28 is sufficient. Decolorizing carbon 28 is added to bottle 26 either before or after the aqueous mixture is transferred into this bottle. Once the decolorizing carbon has been added, bottle 26 is sealed using lid 27, and the capped bottle is shaken vigorously for about one minute. If bottle 26 has a wide enough neck, then it will serve the purpose of beaker 23, thus enabling the macerated plant tissue to be transferred directly from grinder 18 to bottle 26.

Filter funnel 30 has an exit end 32 and is used for filtering the decolorized aqueous mixture. Funnel 30 is illustratively a Buckner funnel, in which case the kit contains filter paper 31, or is a sintered glass funnel. As shown in FIG. 2, funnel 30 is supported during filtration by funnel holder 34, which is directly attached to cover member 13. To exit end 32 of funnel 30, there is attached a syringe 36 having a plunger 38, with the attachment being through the intermediacy of a tube 40. The decolorized aqueous mixture is poured from bottle 26 into funnel 30, and plunger 38 is withdrawn from syringe 36 to apply a vacuum to the decolorized aqueous mixture. The aqueous filtrate is collected in syringe 36.

There is added to each mixing bottle 42 from syringe 36, a quantity of the aqueous filtrate sufficient to fill each mixing bottle 42 to the indicator line 44. Suitably, indicator line 44 represents a 10 ml volume level. If bottle 26 has an indicator line 44, then it will serve the purpose of mixing bottle 42, thus enabling the aqueous filtrate to be transferred to bottle 26 from syringe 36. Mixing bottle 42 may be used in place of graduated flask 25 to measure a 30 ml volume.

To one of mixing bottles 42, containing the aqueous filtrate, there is added a small amount of buffer 46. A sufficient amount of buffer 46 raises the pH of the aqueous filtrate high enough to render the magnesium ions in the aqueous filtrate unavailable during the calcium ion titration step described below. Buffer 46 is advantageously an aqueous solution of an alkali metal hydroxide, with the alkali metal thereof being potassium or sodium. 2–10 N potassium hydroxide is useful as the buffer, with 6–8 N potassium hydroxide being particularly useful. About 2 drops of 8.0 N potassium hydroxide solution is sufficient for the 10 ml volume.

There is also added to the same mixing bottle 42, a colorimetric indicator reagent 48. Exemplary reagents are murexide (ammonium purpurate), Eriochrome Blue Black, Eriochrome Blue Black R, and solochrome dark blue. Each of these indicator reagents imparts the aqueous filtrate with a first color in the presence of calcium ions and with a scond color in the absence of calcium ions. Eriochrome Blue Black R is the sodium salt of 1-(2-hydroxy-1-naphthylazo)-2-naphthol-4-sulfonic acid. At a pH between 11 and 14 this indicator has a red shade in the presence of calcium and is blue when the calcium is completely complexed with the titrant. Reagent 48 is suitably provided by the contents of one Cal-Ver ®II powder pillow, available from Hach Chemical. Buffer 46 and the indicator reagent 48 are added in any order to mixing bottle 42 containing the aqueous filtrate.

After buffer 46 and indicator reagent 48 have been added to mixing vial 42 containing the aqueous filtrate, the aqueous filtrate is titrated for the quantity of calcium ions present using a titrating agent 50. Ethylenediaminetetraacetic acid (EDTA) is advantageously used for this titration. Titrant 50 is added by drops until the desired color change is observed. EDTA is suitably provided as Hardness 3 solution, available from Hach Chemical. When the Hach solution is used, the number of drops required is equal to milliequivalents of calcium ions/100 g. One variation is that a few of the drops of titrant 50 required to bring about the desired color change could be added to mixing vial 42 containing the aqueous filtrate prior to adding buffer 46 and indicator reagent 48, so long as the number of drops added at this time is less than the total number of drops required.

A buffer other than the aqueous solution of an alkali metal hydroxide, an indicating reagent other than those described above, and a titrating agent other than EDTA may be used for determining the quantity of calcium ions present, and in this regard, there is illustratively incorporated by reference into this application the disclosure of U.S. Pat. No. 3,121,613 to Bittner, which uses an alkaline borate solution as the buffer, ethylene glycol bis($\beta$-aminoethylether)-N,N'-tetraacetic acid as the titrating agent, and an Eriochrome Blue Black R-methyl red indicator. The alkaline borate solution is used to adjust the pH to between about 11 and 14. There is also hereby incorporated by reference into this application the disclosure of U.S. Pat. No. 3,798,000 to Helger, which uses other indicator reagents, used a buffer to adjust the pH to between 8.5 and 12, and 8-hydroxyquinoline to mask the magnesium ions.

To the other mixing vial 42 containing the aqueous filtrate, there is added a colorimetric indicator reagent 52 for indicating the presence of both calcium and magnesium ions. Reagent 52 is illustratively calmagite or Eriochrome Black T. Each of these indicator reagents imparts the aqueous filtrate with one color in the presence of calcium and magnesium ions and with another color in the absence of calcium and magnesium ions. Reagent 52 is advantageously provided by the contents of two UniVer® III powder pillows available from Hach Chemical.

After reagent 52 has been added to the other mixing vial 42 containing the aqueous filtrate, the aqueous filtrate is titrated for the quantity of calcium and magnesium ions present using EDTA or any other titrating agent that will titrate both magnesium and calcium. This titrating agent is the same as or different from titrating agent 50. For example, EGTA could be used in titrating calcium, and EDTA could be used in titrating both calcium and magnesium. It is preferable that this titrating agent be the same as agent 52 in order to conserve room in the kit. This titrant is added by drops until the desired color change is seen. When Hardness 3 solution, available from Hach Chemical, is used to supply EDTA titrant, the number of drops required is equal to milliequivalents of calcium and magnesium ion per 100 grams. For this titration the pH of the aqueous filtrate must be about pH7. In the event the pH is not already about 7, an $NH_4OH/NaCl$ buffer may be used to adjust the filtrate to this pH.

One modification is that a few drops of the titrant used for both the calcium and magnesium ions could be added to the other mixing vial 42 containing the aqueous filtrate prior to adding indicator reagent 52, so long as the number of drops added at this time is less than the total number of drops required.

In this disclosure, there is shown and essentially described only the preferred embodiment of the invention. It is to be understood that the invention is capable of changes or modifications within the scope of the inventive concept expressed herein. Several of these obvious changes or modifications have been briefly mentioned for purposes of illustration.

Examples showing the use of the test kit of the present invention for field analysis of the magnesium content of plant tissue are set forth below. These examples are merely illustrative of how this test kit is used.

EXAMPLE 1

Using a number 14 cork borer, one plug is taken from each of 20 soybean leaves. The 20 leaf plugs provide a sample that is approximately 1 gram in weight. The leaf plugs are placed in the grinder shown in the drawing and thoroughly ground, and the ground leaf tissue is scraped and washed with 30 ml of deionized water into a beaker. The aqueous mixture is poured from the beaker into a plastic bottle to which two scoops of decolorizing carbon are added using a microspatula. The bottle is capped and shaken vigorously for one minute, and the mixture is filtered using a Buchner funnel that is supported by a funnel holder that is attached to the vertical lid of the test kit container. A vacuum is applied to the aqueous mixture by withdrawing the plunger of a syringe that is attached by means of a tube to the exit end of the Buchner funnel.

10 ml of the aqueous filtrate is transferred from the syringe to each of two bottles. To one of these bottles there is added two drops of 8.0 N potassium hydroxide solution and the contents of one CalVer®II powder pillow, available from Hach Chemical. The resulting solution is mixed by swirling, and to the swirled red solution, there is added by drops Hardness 3 solution, available from Hach Chemical, until the color changes from red to pure blue. To the second bottle containing the aqueous filtrate, there is added the contents of two UniVer®III powder pillows, available from Hach Chemical, and the resulting solution is mixed by swirling. To the swirled red solution, there is added by drops Hardness 3 solution until the color changes from red to blue.

The number of drops used in the first titration is subtracted from the number of drops used in the second titration, and the difference is multiplied by 1105 to give ppm magnesium.

The above procedure is repeated seven times, and the average value for eight runs is 2003 Mg±5%. The value obtained by ashing the sample, dissolving the ashes and analyzing by atomic absorption (AA) is 1939 ppm Mg±14% (average for eight runs). By dividing the average AA result by the average test kit result, there is obtained a factor of 0.97. Multiplication of the test kit result by this factor yields a value that is the same as if the analysis had been by AA in the laboratory.

EXAMPLE 2

Following the procedure of Example 1 except that corn leaves are used rather than soybean leaves, 1874 ppm Mg±22% (average for eight runs) is found present. Using AA analysis, 1590 ppm Mg±7% (average for eight runs) is determined to be in the leaves. The conversion factor is 0.85 (1590 divided by 1874).

Industrial Applicability

This invention is useful for field analysis of the magnesium and calcium content of plant tissue. Magnesium in several ways is to a plant as iron is to the human body. It aids in the manufacture of chlorophyll, in fruit production and in the utilization of other nutrients. Without magnesium the plant will grow pale green and probably die. Magnesium is particularly used by the plant when under stress, for example, when the plant is growing, flowering, making seed or in the need of water.

We claim:

1. A portable test kit for field analysis of the magnesium and calcium content of plant tissue, said kit comprising:
    a test kit container having a base member, a cover member and a means that maintains said cover member vertical when said container is fully opened;
    means for sampling plant tissue;
    means for particulating the plant tissue sample;
    at least one reservoir container into which the particulated plant tissue is transferred, the transfer being accomplished by use of a measured quantity of a deionized aqueous solvent whereby there is formed in said reservoir container an aqueous mixture of said particulated plant tissue;
    demineralizing means for forming said deionized aqueous solvent from an aqueous solvent;
    at least one reservoir vial having a lid means, into which said aqueous mixture is transferred from said reservoir container;
    means for decolorizing a liquid sample, a part of said decolorizing means being chargeable to said reservoir vial to remove the color from said aqueous mixture;
    means for filtering the decolorized aqueous mixture;
    means for supporting said filtering means during filtration, said supporting means being directly attachable to said cover member;
    means for exerting a vacuum on the decolorized aqueous mixture during filtration, and for collecting the aqueous filtrate;
    at least two mixing vials each having an indicator line, into which there is transferred from said vacuum-exerting and filtrate-collecting means a quantity of said aqueous filtrate sufficient to fill each mixing vial to said indicator line; at least one means for buffering said aqueous filtrate, said buffering means rendering magnesium ions unavailable during calcium ion titration; a portion of said buffering means being chargeable to one of said at least two mixing vials containing said aqueous filtrate;
    at least one means for colorimetrically indicating the presence of calcium ions and being a first indicating means; a portion of said first indicating means being chargeable to said one of said at least two mixing vials, and imparting said aqueous filtrate with a first color in the presence of calcium ions and with a second color in the absence of calcium ions;
    at least one means for titrating the quantity of calcium ions present, a portion of said calcium ion titrating means being introduceable into said one of said at least two mixing vials, into which said portion of said buffer means and said portion of said first indicator means is charged;
    at least one means for colorimetrically indicating the presence of both calcium and magnesium ions and being a second indicator means; a portion of said second indicator means being introduceable into the other of said at least two mixing vials containing said aqueous filtrate, and imparting said aqueous filtrate with one color in the presence of calcium and magnesium ions and with another color in the absence of calcium and magnesium ions; and
    at least one means for titrating the quantity of both calcium and magnesium ions present, a portion of said calcium and magnesium ion titrating means being chargeable to said other of said at least two mixing vials, into which said portion of said second indicating reagent is introduced.

2. The test kit of claim 1 wherein said deionized aqueous solution is deionized water.

3. The test kit of claim 1 wherein said decolorizing means is decolorizing carbon.

4. The test kit of claim 1, wherein said vacuum-exerting and filtrate-collecting means comprises a syringe attachable to the exit end of said filtering means through th intermediacy of a hollow connecting member, said syringe exerting said vacuum upon withdrawal of the plunger thereof.

5. The test kit of claim 1 wherein said buffering means is an aqueous solution of an alkali metal hydroxide, said alkali metal being potassium or sodium.

6. The test kit of claim 5 wherein said aqueous solution of an alkali metal hydroxide is about 6-8 N potassium hydroxide.

7. The test kit of claim 1 wherein said first indicating means comprises a dye selected from the group consisting of murexide, Eriochrome Blue Black, Eriochrome Blue Black R and solochrome dark blue.

8. The test kit of claim 1 wherein said second indicating means comprises a dye selected from the group consisting of calmagite and Eriochrome Black T.

9. The test kit of claim 1 wherein said calcium and magnesium ion titrating means and said calcium ion titrating means are the same.

10. The test kit of claim 9 wherein said calcium and magnesium ion titrating means and said calcium ion titrating means are ethylenediaminetetraacetic acid.

11. The test kit of claim 1, wherein said means for sampling plant tissue is a cork borer.

12. The test kit of claim 4, wherein said deionized aqueous solution is deionized water; wherein said decolorizing means is decolorizing carbon; wherein said buffering means is about 6-8 N potassium hydroxide; wherein said first indicating means comprises a dye selected from the group consisting of murexide, Eriochrome Blue Black, Eriochrome Blue Black R and solochrome dark blue; wherein said second indicating means comprises a dye selected from the group consisting of calmagite and Eriochrome Black T; wherein said calcium and magnesium ion titrating means and said calcium ion titrating means are ethylenediaminetetraacetic acid; wherein said means for sampling plant tissue is a cork borer; and wherein said particulating means is a grinder.

13. The test kit of claim 1, wherein said particulating means is a grinder.

* * * * *